United States Patent [19]
Ressemann et al.

[11] Patent Number: 6,155,264
[45] Date of Patent: Dec. 5, 2000

[54] PERCUTANEOUS BYPASS BY TUNNELING THROUGH VESSEL WALL

[75] Inventors: Thomas V. Ressemann, St. Cloud; Kent D. Harrison, Maple Grove, both of Minn.

[73] Assignee: Scimed Life Systems, Inc., Maple Grove, Minn.

[21] Appl. No.: 08/812,879

[22] Filed: Mar. 6, 1997

[51] Int. Cl.$^7$ .................................................. A61B 19/00
[52] U.S. Cl. ............................................. 128/898; 604/49
[58] Field of Search ................... 623/2, 3, 900; 604/96, 4, 9, 52; 606/194, 6–7; 600/16

[56] References Cited

U.S. PATENT DOCUMENTS

| | | |
|---|---|---|
| Re. 35,352 | 10/1996 | Peters . |
| Re. 35,459 | 2/1997 | Junkman . |
| 3,667,069 | 6/1972 | Blackshear et al. . |

(List continued on next page.)

FOREIGN PATENT DOCUMENTS

| | | |
|---|---|---|
| 0 769 272 A1 | 4/1997 | European Pat. Off. . |
| 97-281410 | 7/1997 | Japan . |
| 308752 | 7/1971 | U.S.S.R. . |
| 388738 | 9/1971 | U.S.S.R. . |
| 891076 | 12/1981 | U.S.S.R. . |
| 1822750 A1 | 7/1982 | U.S.S.R. . |
| 1600708 | 12/1995 | U.S.S.R. . |
| WO 95/08364 | 3/1995 | WIPO . |
| WO 95/10218 | 4/1995 | WIPO . |
| WO 95/15192 | 6/1995 | WIPO . |
| WO 95/16476 | 6/1995 | WIPO . |

(List continued on next page.)

OTHER PUBLICATIONS

"The Current Status of Lasers in the Treatment of Cardiovascular Disease" by Jeffrey M. Isner and Richard H. Clarke, *IEEE*, vol. QE–20, No. 12, Dec. 1984, pp. 1406–1420.

"The Possibility of Myocardial Revascularization by Creation of a Left Ventriculocoronary Artery Fistula", by Ian Munro and Peter Allen, M.D., *Journal of Thoracic and Cardiovascular Surgery*, vol. 58, No. 1, Jul. 1969, pp. 25–32.

Isner et al. "The Current Status of Lasers in the Treatment of Cardiovascular Disease" J. Quantum Electronics:QE–20(12): pp. 1406–1420, Dec. 1984.

*Primary Examiner*—Mickey Yu
*Assistant Examiner*—Kelly O'Hara
*Attorney, Agent, or Firm*—Westman, Champlin & Kelly, P.A.

[57] ABSTRACT

A parent vessel lies adjacent heart tissue, and a restriction in the parent vessel is bypassed. A first region of the parent vessel on a first side of the restriction is accessed and an aperture is formed therein. A lumen is formed through the heart tissue, and the lumen communicates with the parent vessel through the first aperture. A second aperture is formed in a second region of the parent vessel on a second side of the restriction. The lumen through the heart tissue communicates with the parent vessel through the first and second apertures, thus bypassing the restriction.

19 Claims, 6 Drawing Sheets

U.S. PATENT DOCUMENTS

| | | |
|---|---|---|
| 4,016,884 | 4/1977 | Kwan-Gett . |
| 4,165,747 | 8/1979 | Bermant . |
| 4,173,981 | 11/1979 | Mortensen . |
| 4,190,909 | 3/1980 | Ablaza . |
| 4,230,096 | 10/1980 | Zeff et al. . |
| 4,546,499 | 10/1985 | Possis et al. . |
| 4,562,597 | 1/1986 | Possis et al. . |
| 4,566,453 | 1/1986 | Kumano et al. . |
| 4,601,718 | 7/1986 | Possis et al. . |
| 4,610,661 | 9/1986 | Possis et al. . |
| 4,667,673 | 5/1987 | Li . |
| 4,690,684 | 9/1987 | McGreevy et al. . |
| 4,710,192 | 12/1987 | Liotta et al. . |
| 4,721,109 | 1/1988 | Healey . |
| 4,790,819 | 12/1988 | Li et al. . |
| 4,803,984 | 2/1989 | Narayanan et al. . |
| 4,808,163 | 2/1989 | Laub . |
| 4,819,640 | 4/1989 | Narayanan et al. . |
| 4,827,931 | 5/1989 | Longmore . |
| 4,907,591 | 3/1990 | Vasconcellos et al. . |
| 4,911,164 | 3/1990 | Roth . |
| 4,995,857 | 2/1991 | Arnold . |
| 5,011,469 | 4/1991 | Buckberg et al. . |
| 5,037,428 | 8/1991 | Picha et al. . |
| 5,047,039 | 9/1991 | Avant et al. . |
| 5,053,041 | 10/1991 | Ansari et al. . |
| 5,053,043 | 10/1991 | Gottesman et al. . |
| 5,061,245 | 10/1991 | Waldvogel . |
| 5,067,958 | 11/1991 | Sandhaus . |
| 5,080,663 | 1/1992 | Mills et al. . |
| 5,080,664 | 1/1992 | Jain . |
| 5,104,402 | 4/1992 | Melbin . |
| 5,144,961 | 9/1992 | Chen et al. . |
| 5,222,962 | 6/1993 | Burkhart . |
| 5,222,963 | 6/1993 | Brinkerhoff et al. . |
| 5,222,971 | 6/1993 | Willard et al. . |
| 5,234,445 | 8/1993 | Walker et al. . |
| 5,254,113 | 10/1993 | Wilk . |
| 5,281,236 | 1/1994 | Bagnato et al. . |
| 5,282,810 | 2/1994 | Allen et al. . |
| 5,287,861 | 2/1994 | Wilk . |
| 5,308,320 | 5/1994 | Safar et al. . |
| 5,314,436 | 5/1994 | Wilk . |
| 5,314,472 | 5/1994 | Fontaine . |
| 5,323,789 | 6/1994 | Berggren et al. . |
| 5,330,486 | 7/1994 | Wilk . |
| 5,370,683 | 12/1994 | Fontaine . |
| 5,382,257 | 1/1995 | Lewis et al. . |
| 5,383,854 | 1/1995 | Safar et al. . |
| 5,383,928 | 1/1995 | Scott et al. . |
| 5,397,345 | 3/1995 | Lazarus . |
| 5,403,333 | 4/1995 | Kaster et al. . |
| 5,409,019 | 4/1995 | Wilk .......................................... 128/898 |
| 5,425,705 | 6/1995 | Evard et al. . |
| 5,425,739 | 6/1995 | Jessen . |
| 5,429,144 | 7/1995 | Wilk . |
| 5,433,700 | 7/1995 | Peters . |
| 5,437,684 | 8/1995 | Calabrese et al. . |
| 5,441,507 | 8/1995 | Wilk . |
| 5,443,497 | 8/1995 | Venbrux . |
| 5,447,512 | 9/1995 | Wilson et al. . |
| 5,449,372 | 9/1995 | Schmaltz et al. . |
| 5,452,733 | 9/1995 | Sterman et al. . |
| 5,456,714 | 10/1995 | Owen . |
| 5,472,404 | 12/1995 | Volgushev . |
| 5,501,698 | 3/1996 | Roth et al. . |
| 5,522,884 | 6/1996 | Wright . |
| 5,527,319 | 6/1996 | Green et al. . |
| 5,527,324 | 6/1996 | Krantz et al. . |
| 5,536,251 | 7/1996 | Evard et al. . |
| 5,540,677 | 7/1996 | Sinofsky . |
| 5,540,701 | 7/1996 | Sharkey et al. . |
| 5,545,171 | 8/1996 | Sharkey et al. . |
| 5,554,162 | 9/1996 | DeLange . |
| 5,556,414 | 9/1996 | Turi . |
| 5,556,428 | 9/1996 | Shah . |
| 5,562,728 | 10/1996 | Lararus et al. . |
| 5,569,272 | 10/1996 | Reed et al. . |
| 5,569,274 | 10/1996 | Rapacki et al. . |
| 5,571,090 | 11/1996 | Sherts . |
| 5,571,215 | 11/1996 | Sterman et al. . |
| 5,584,803 | 12/1996 | Stevens et al. . |
| 5,588,949 | 12/1996 | Taylor et al. . |
| 5,591,179 | 1/1997 | Edelstein . |
| 5,591,212 | 1/1997 | Keimel . |
| 5,593,424 | 1/1997 | Northrup, III . |
| 5,601,576 | 2/1997 | Garrison . |
| 5,601,581 | 2/1997 | Fogarty et al. . |
| 5,609,598 | 3/1997 | Laufer et al. . |
| 5,613,937 | 3/1997 | Garrison et al. . |
| 5,618,270 | 4/1997 | Orejola . |
| 5,643,292 | 7/1997 | Hart . |
| 5,653,744 | 8/1997 | Khouri . |
| 5,655,548 | 8/1997 | Nelson et al. ........................... 128/898 |
| 5,662,124 | 9/1997 | Wilk ........................................ 128/898 |
| 5,662,711 | 9/1997 | Douglas . |
| 5,676,670 | 10/1997 | Kim . |
| 5,682,906 | 11/1997 | Sterrman et al. . |
| 5,685,857 | 11/1997 | Negus et al. . |
| 5,693,083 | 12/1997 | Baker et al. . |
| 5,702,368 | 12/1997 | Stevens et al. . |
| 5,702,412 | 12/1997 | Popov et al. . |
| 5,715,832 | 2/1998 | Koblish et al. . |
| 5,716,367 | 2/1998 | Koike et al. . |
| 5,718,725 | 2/1998 | Sterman et al. . |
| 5,722,426 | 3/1998 | Kolff . |
| 5,725,537 | 3/1998 | Green et al. . |
| 5,727,569 | 3/1998 | Benetti et al. . |
| 5,728,151 | 3/1998 | Garrison et al. . |
| 5,735,290 | 4/1998 | Sterman et al. . |
| 5,738,649 | 4/1998 | Macoviak . |
| 5,738,652 | 4/1998 | Boyd et al. . |
| 5,749,892 | 5/1998 | Vierra et al. . |
| 5,752,526 | 5/1998 | Cosgrove . |
| 5,755,682 | 5/1998 | Knudson et al. . |
| 5,755,687 | 5/1998 | Donlon . |
| 5,755,778 | 5/1998 | Kleshinski . |
| 5,758,663 | 6/1998 | Wilk et al. . |
| 5,766,151 | 6/1998 | Valley et al. . |
| 5,769,812 | 6/1998 | Stevens et al. . |
| 5,792,094 | 8/1998 | Stevens et al. . |
| 5,795,325 | 8/1998 | Valley et al. . |
| 5,797,920 | 8/1998 | Kim . |
| 5,797,933 | 8/1998 | Snow et al. . |
| 5,799,661 | 9/1998 | Boyd et al. . |
| 5,800,450 | 9/1998 | Lary et al. . |
| 5,800,522 | 9/1998 | Campbell et al. . |
| 5,836,311 | 11/1998 | Borst et al. .............................. 128/897 |
| 5,849,036 | 10/1998 | Zarate ......................................... 623/1 |
| 5,855,210 | 1/1999 | Sterman et al. ....................... 128/898 |
| 5,855,614 | 1/1999 | Stevens et al. ........................... 623/11 |
| 5,868,770 | 2/1999 | Rygaard ................................. 606/167 |

FOREIGN PATENT DOCUMENTS

| | | |
|---|---|---|
| WO 96/10375 | 4/1996 | WIPO . |
| WO 96/17644 | 6/1996 | WIPO . |
| WO 96/25886 | 8/1996 | WIPO . |
| WO 96/30072 | 10/1996 | WIPO . |
| WO 96/30073 | 10/1996 | WIPO . |
| WO 96/32882 | 10/1996 | WIPO . |
| WO 97/12555 | 4/1997 | WIPO . |
| WO 97/13463 | 4/1997 | WIPO . |

| | | | | | | |
|---|---|---|---|---|---|---|
| WO 97/13468 | 4/1997 | WIPO . | | WO 98/19634 | 5/1998 | WIPO . |
| WO 97/13471 | 4/1997 | WIPO . | | WO 98/19636 | 5/1998 | WIPO . |
| WO 97/26939 | 7/1997 | WIPO . | | WO 98/31302 | 7/1998 | WIPO . |
| WO 97/37984 | 10/1997 | WIPO . | | WO 98/32380 | 7/1998 | WIPO . |
| WO 97/40751 | 11/1997 | WIPO . | | WO 98/35626 | 8/1998 | WIPO . |
| WO 98/06356 | 2/1998 | WIPO . | | WO 98/37814 | 9/1998 | WIPO . |
| WO 98/07399 | 2/1998 | WIPO . | | WO 98/51223 | 11/1998 | WIPO . |
| WO 98/10714 | 3/1998 | WIPO . | | WO 98/52474 | 11/1998 | WIPO . |
| WO 98/15237 | 4/1998 | WIPO . | | WO 98/52475 | 11/1998 | WIPO . |
| WO 98/16161 | 4/1998 | WIPO . | | WO 98/57590 | 12/1998 | WIPO . |
| WO 98/16174 | 4/1998 | WIPO . | | WO 98/57591 | 12/1998 | WIPO . |
| WO 98/17182 | 4/1998 | WIPO . | | WO 98/57592 | 12/1998 | WIPO . |
| WO 98/17187 | 4/1998 | WIPO . | | WO 99/04836 | 2/1999 | WIPO . |
| WO 98/19607 | 5/1998 | WIPO . | | WO 99/04845 | 2/1999 | WIPO . | though hard, it can be quite difficult, if not impossible, to cross the
PERCUTANEOUS BYPASS BY TUNNELING THROUGH VESSEL WALL

INCORPORATION BY REFERENCE

The following U.S. patent applications are hereby fully incorporated:

U.S. patent application Ser. No. 08/813,038 filed on Mar. 6, 1997, entitled SYSTEM AND METHOD FOR PERCUTANEOUS CORONARY ARTERY BYPASS, filed on even date herewith and assigned to the same assignee as the present application; and U.S. patent application Ser. No. 08/813,040 filed on Mar. 6, 1997, entitled PERCUTANEOUS BYPASS WITH BRANCHING VESSEL, filed on even date herewith and assigned to the same assignee as the present application.

BACKGROUND OF THE INVENTION

The present invention generally deals with vascular bypass methods. More specifically, the present invention deals with systems for performing percutaneous coronary artery bypass procedures.

Coronary arteries can become partially restricted (stenotic) or completely clogged (occluded) with plaque, thrombus, or the like. This reduces the efficiency of the heart, and can ultimately lead to a heart attack. Thus, a number of different systems and methods have been developed for treating stenotic or occluded coronary arteries.

Two methods which have been developed to treat occlusions and stenoses include balloon angioplasty and pharmacological treatment. However, where the occlusion is quite hard, it can be quite difficult, if not impossible, to cross the occlusion with an angioplasty device. In addition, some coronary stenoses are too diffuse to treat effectively with balloon angioplasty. Unfortunately, such occlusions are not readily susceptible to dissolution with chemicals either. In the past, patients with these types of occlusions have been candidates for open heart surgery to bypass the restrictions.

However, open heart surgery includes a myriad of disadvantages. Open heart surgery typically includes a great deal of postoperative pain. The pain is normally encountered because conventional open heart surgery requires that the sternum be cracked open, which is quite painful. Also, open heart surgery typically involves bypassing the occluded vessel, which, in turn, involves harvesting a vein from another part of the body for use as the bypass graft. One common source for the bypass graft is the saphenous vein which is removed from the leg. Harvesting the saphenous vein requires the surgeon to cut and peel the skin back from an area of the leg which is approximately 18 inches long and which extends upward to the groin area. This can be very traumatic and painful. Also, the internal mammary artery (IMA) has also been used as a vein graft in performing a bypass. However, the IMA is typically best suited for use as a left anterior descending (LAD) vein graft and is commonly saved for that purpose. Further, open heart surgery requires quite a lengthy recovery period which involves an increased hospital stay, and, consequently, greater expense.

Other than the pain and more lengthy hospital stay, open heart surgery involves other disadvantages as well. For example, during open heart surgery, it is common to cool the heart to a point where it stops. The blood from the remainder of the vasculature is then pumped through a pulmonary and cardiac bypass system. Any time the heart is stopped, there is a danger of encountering difficulty in restarting the heart (which is typically accomplished by warming the heart and massaging it). Further, even if the heart is restarted, it sometimes does not return to a correct rhythm. Also, open heart surgery can require the use of a device known as a left ventricular assist device (LVAD) to supplementarily pump blood to relieve the burden on the heart. This allows the heart to heal.

A significant reason that the heart is typically stopped during open heart surgery is that, if it were not stopped, the surgeon would be working in a dynamic environment. In such an environment, the target vessels and tissue to be treated are moving. Further, a system must be employed in such an environment to stop bleeding. Clinical studies indicate that, when blood flow is stopped using clamping devices and blood flow is diverted to a cardiac bypass system, a statistically significant instance of neurological problems caused by blood clotting results. The use of mechanical clamps to stop blood flow, and the use of a mechanical bypass system, results in an approximate six percent instance of neurological problems, such as stroke, memory failure, etc.

Given the difficulties of the techniques discussed above, another approach has been developed which does not require stoppage of the heart or an open chest during execution. This approach is to perform a bypass using a minimally invasive technique by entering the upper chest cavity, through a hole between ribs, under visual observation. Such a technique is often referred to as minimally invasive direct coronary artery bypass (MIDCAB) (where the heart is not stopped) or heart port (where the heart is stopped). Such a system which is used to perform a bypass is disclosed in the Sterman et al. U.S. Pat. No. 5,452,733.

SUMMARY OF THE INVENTION

A parent vessel lies adjacent heart tissue, and a restriction in the parent vessel is bypassed. A first region of the parent vessel on a first side of the restriction is accessed and an aperture is formed therein. A lumen is formed through the heart tissue, and the lumen communicates with the parent vessel through the first aperture. A second aperture is formed in a second region of the parent vessel on a second side of the restriction. The lumen through the heart tissue communicates with the parent vessel through the first and second apertures, thus bypassing the restriction.

DETAILED DESCRIPTION OF THE PREFERRED EMBODIMENTS

Figure 1A:
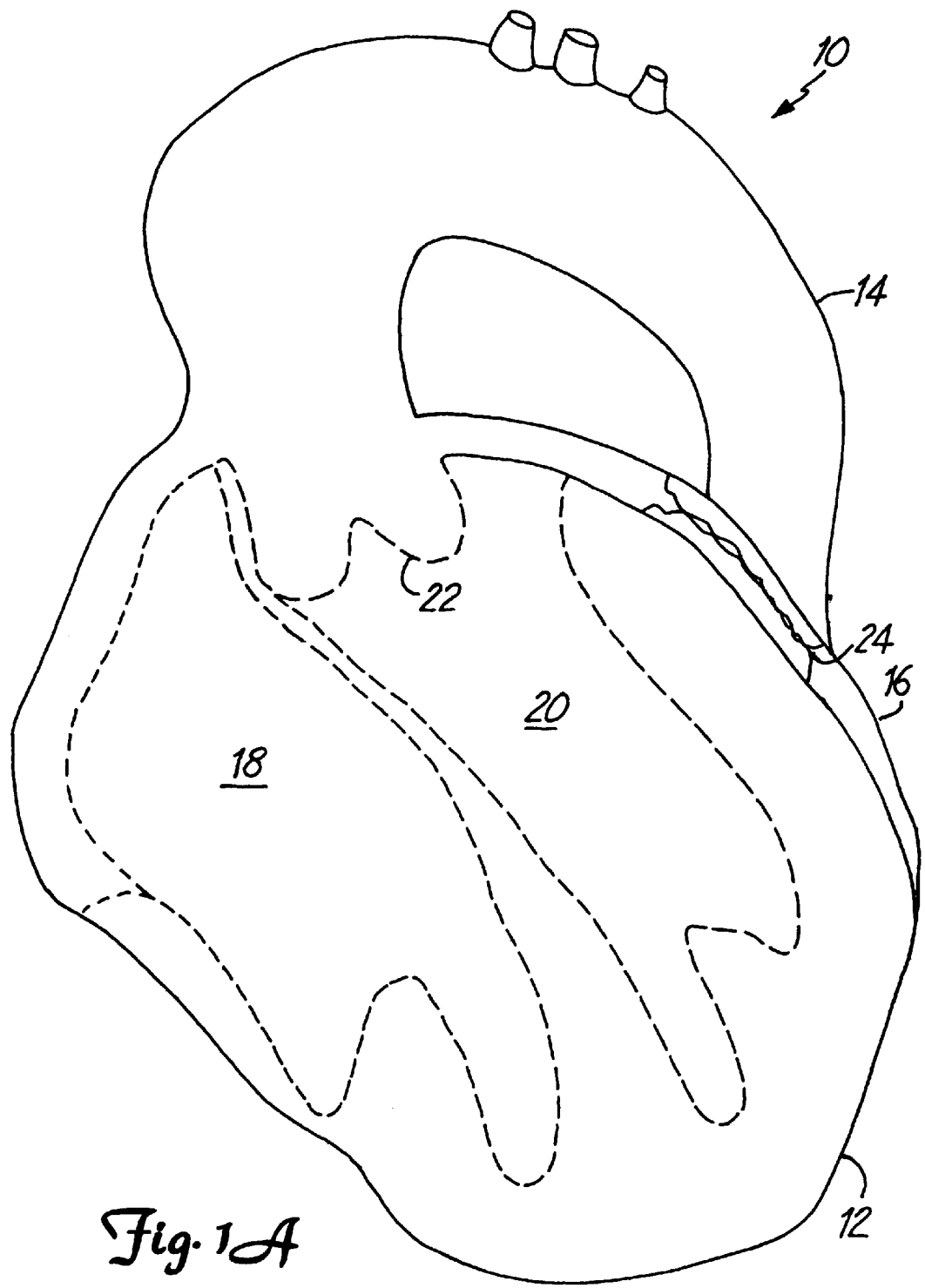
FIG. 1A illustrates a portion of a coronary vascular system with an artery having a restriction.

FIG. 1A illustrates a portion of a vascular system 10 including heart 12, aorta 14, and an artery 16. FIG. 1 also illustrates a plurality of chambers 18 and 20 in heart 12, and a valve 22. A restriction 24 is illustrated in artery 16.

Figure 1B:
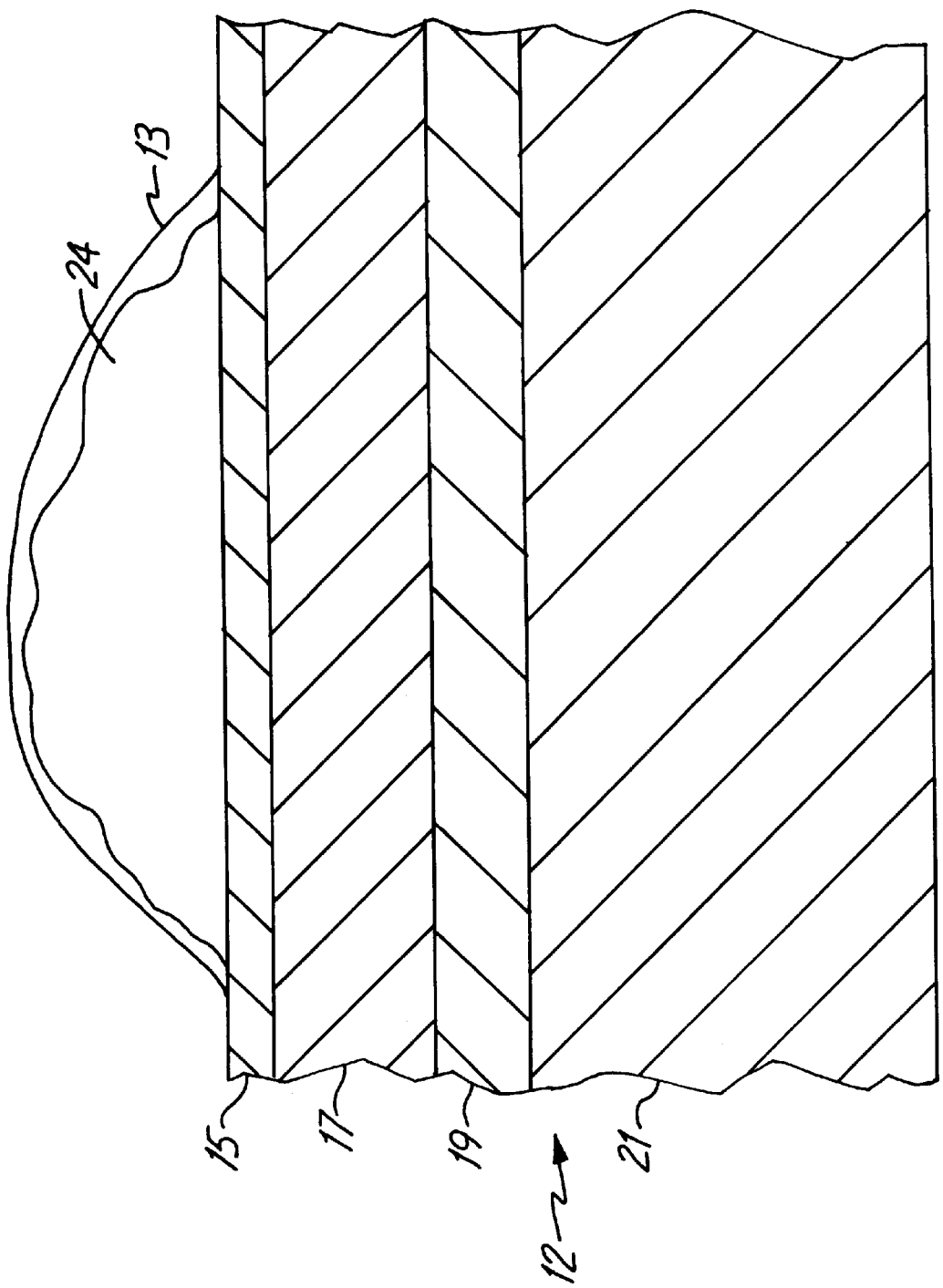
FIG. 1B illustrates a greatly enlarged crosssectional view of a portion of the heart and artery shown in FIG. 1A in the area of the restriction.

FIG. 1B is a greatly enlarged cross-sectional view of a portion of heart 12, and vessel 16 in the area of restriction 24. FIG. 1B illustrates that restriction 24 is typically covered within vessel 16 by an endothelial cell layer 13. Also, the wall of artery 16, and the heart tissue adjacent the wall of artery 16 is made up of a plurality of layers including internal elastic lamina (IEL) 15, media 17, adventitia 19, and myocardium 21. Typically, the depth of the IEL layer 15, media layer 17 and adventitia layer 19, together, is approximately 1 mm. Also, typically, the thickness of the myocardium layer 21 is approximately 5–10 mm. The present invention bypasses restriction 24 by tunneling around restriction 24 through the layers of artery 16, and heart 12. It should specifically be noted that the present invention, when referring to boring or tunneling through heart tissue, contemplates that restriction 24 can be bypassed by tunneling around it through myocardium layer 21, or short of myocardium layer 21, and through one or more of IEL layer 15, media layer 17 and adventitia layer 19. Thus, the path of the tunnel around restriction 24 need not pierce all the way to myocardium layer 21.

Figure 2:
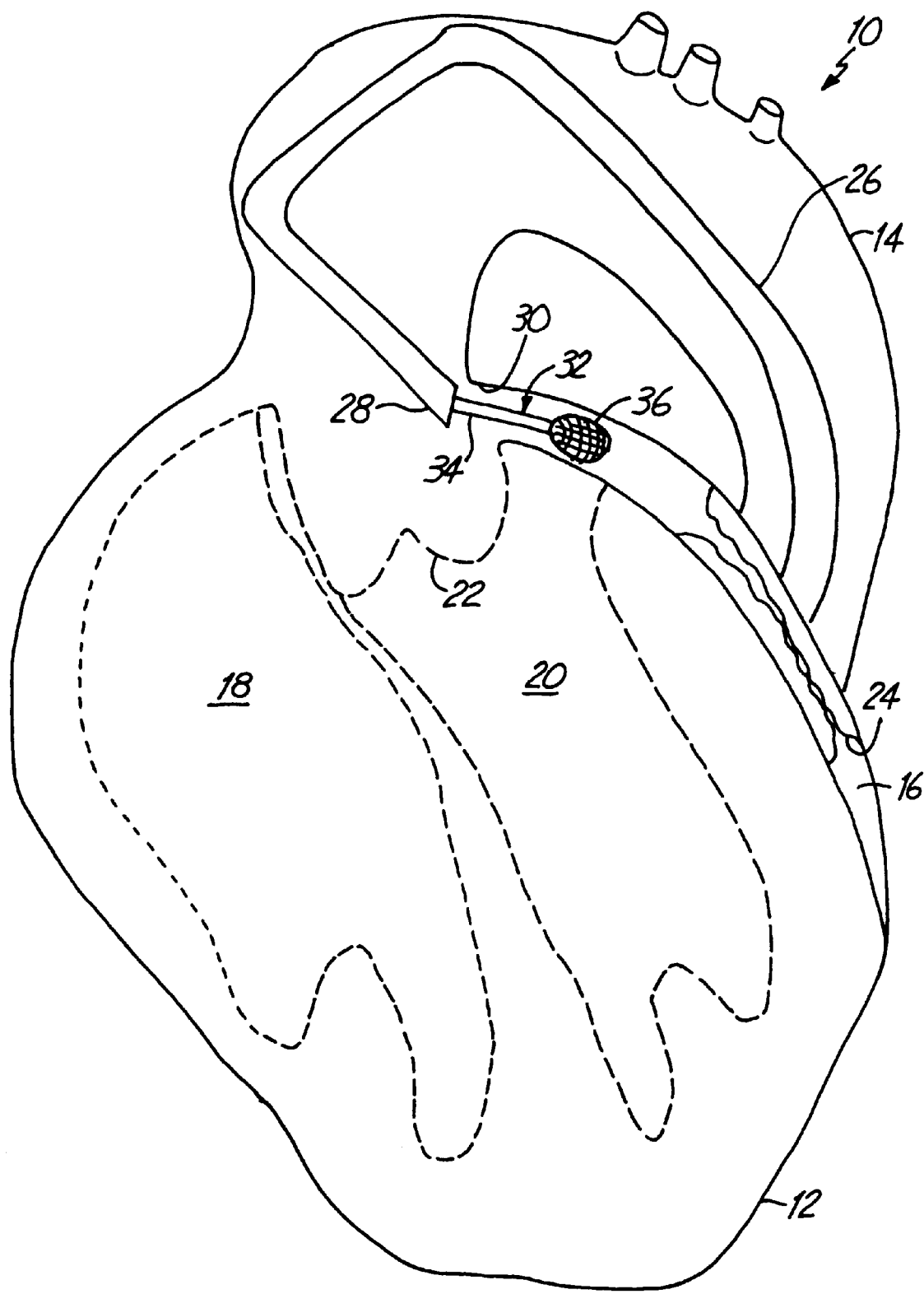
FIG. 2. illustrates a boring device accessing a region proximal of the restriction.

FIG. 2 illustrates a first step utilized in accordance with the present invention to bypass restriction 24 in artery 16. A standard guide catheter 26 is advanced through aorta 14 in a known manner. Guide catheter 26 is positioned such that its distal end 28 is located in a region proximate the ostium 30 of artery 16. Cutting device 32 is then advanced through guide catheter 26, out through distal end 28 of guide catheter 26, through ostium 30 of vessel 16 and to a region proximal of restriction 24 in vessel 16. Cutting device 32, in the preferred embodiment, includes a catheter portion 34 and a boring or cutting member 36. Boring or cutting member 36 can take any number of suitable forms, such as a rotatable member or blade which can be used in piercing and boring through tissue. It should be noted that cutting device 32 can be any suitable mechanical cutting device, or any suitable sort of energy device, such as a radio frequency (RF) ablation wire, or a laser, or other device.

Figure 3:
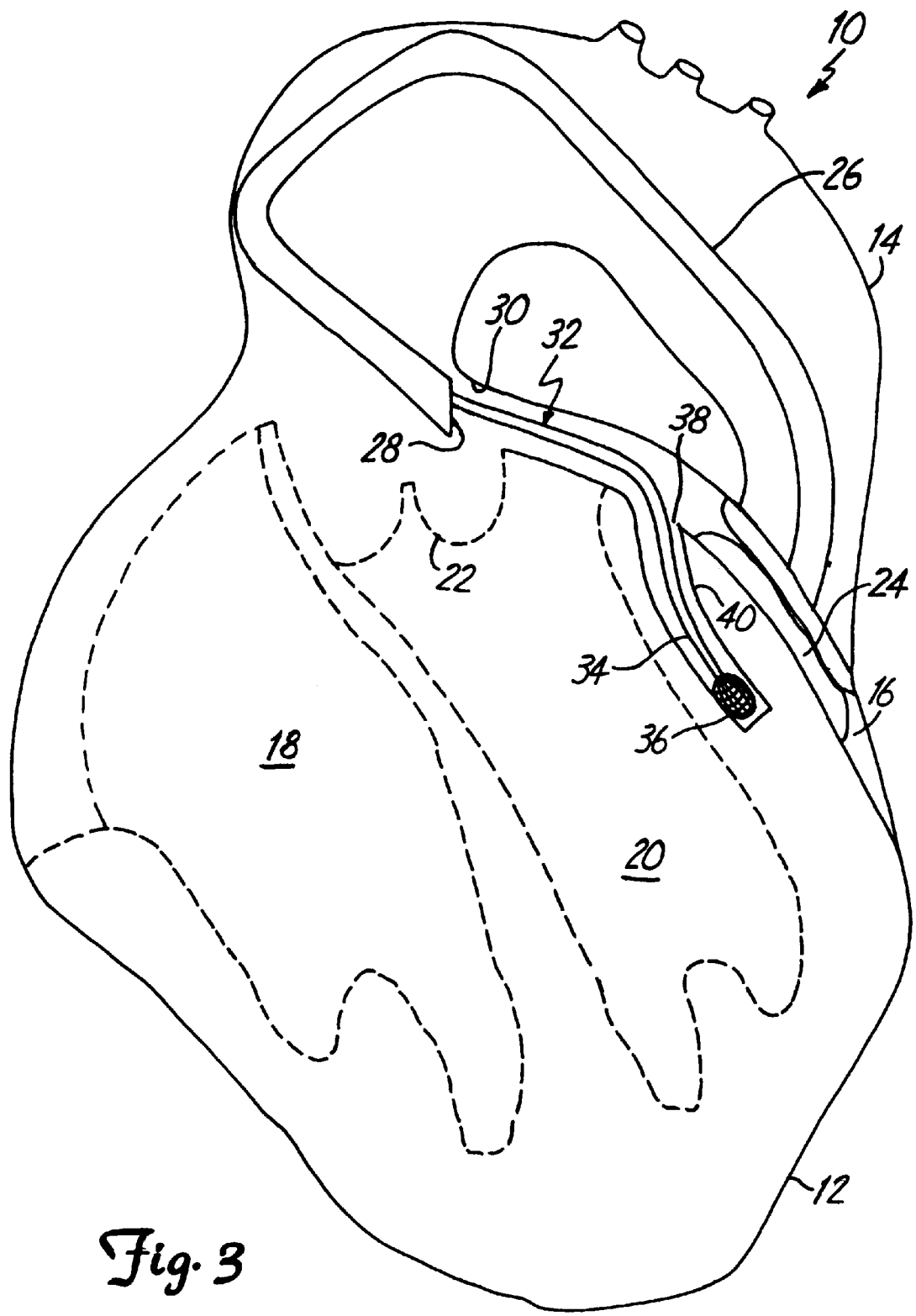
FIG. 3 illustrates the boring device forming a lumen through heart tissue.

FIG. 3 illustrates an additional step utilized in accordance with the present invention in bypassing restriction 24 in vessel 16. Cutting device 32 is advanced to the region proximal of restriction 24 in vessel 16. Cutting member 36 is then used to pierce the wall of vessel 16 to form an aperture 38 in the region proximal of restriction 24. Alternatively, cutting device 32 can be used to create another ostium in aorta 14 preferably in a region proximate the ostium of vessel 16. In that case, cutting device 32 need not be advanced into vessel 16. In either case, cutting device 32 is then further advanced through the myocardium 21 (or only through any or all of the other tissue layers 15, 17 and 19) closely proximate vessel 16. In one preferred embodiment, cutting device 32 is advanced such that lumen 40 is generally parallel to lumen 16 in the region proximate restriction 24.

Figure 4:
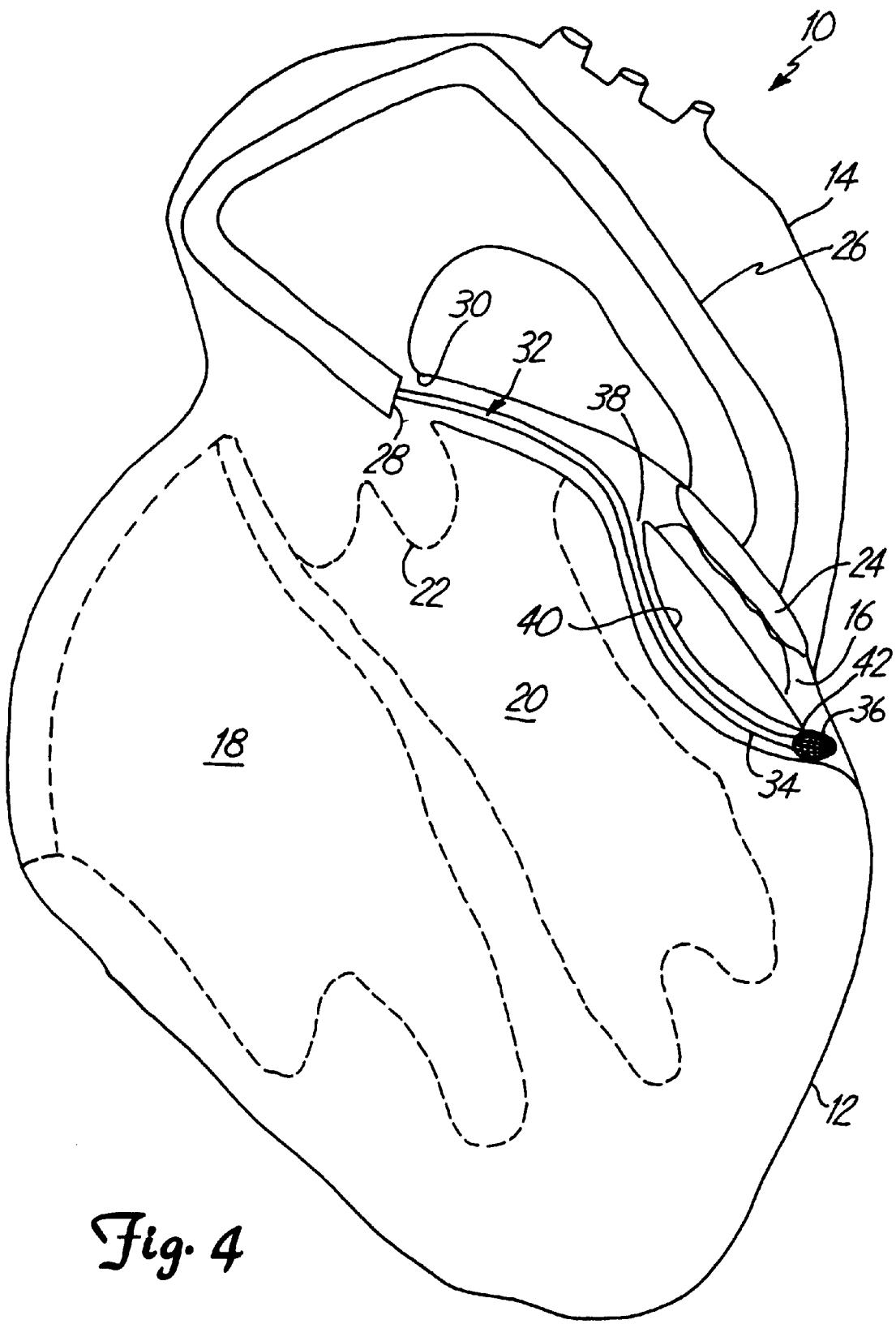
FIG. 4 illustrates the boring device shown in FIG. 3 extending the lumen through the heart tissue into a region of the artery distal of the restriction.

FIG. 4 illustrates yet another step utilized in accordance with one preferred embodiment of the present invention for bypassing restriction 24 in vessel 16. FIG. 4 illustrates that, in the preferred embodiment, cutting device 32 is advanced such that cutting tip 36 advances through lumen 40 in the heart tissue to again pierce the vessel wall of vessel 16 to form a second aperture 42 therein. Second aperture 42 is located distal of restriction 24. In this way, lumen 40 extends from aperture 38 (proximal of restriction 24) to aperture 42 (distal of restriction 24) such that lumen 40 bypasses restriction 24 in vessel 16.

In a preferred embodiment, aspiration is provided during the cutting operation to remove severed tissue pieces. Such aspiration is preferably accompanied by saline infusate to flush the area around cutting tip 36. Aspiration can be provided using any suitable known technique, such as an aspiration catheter.

Figure 5:
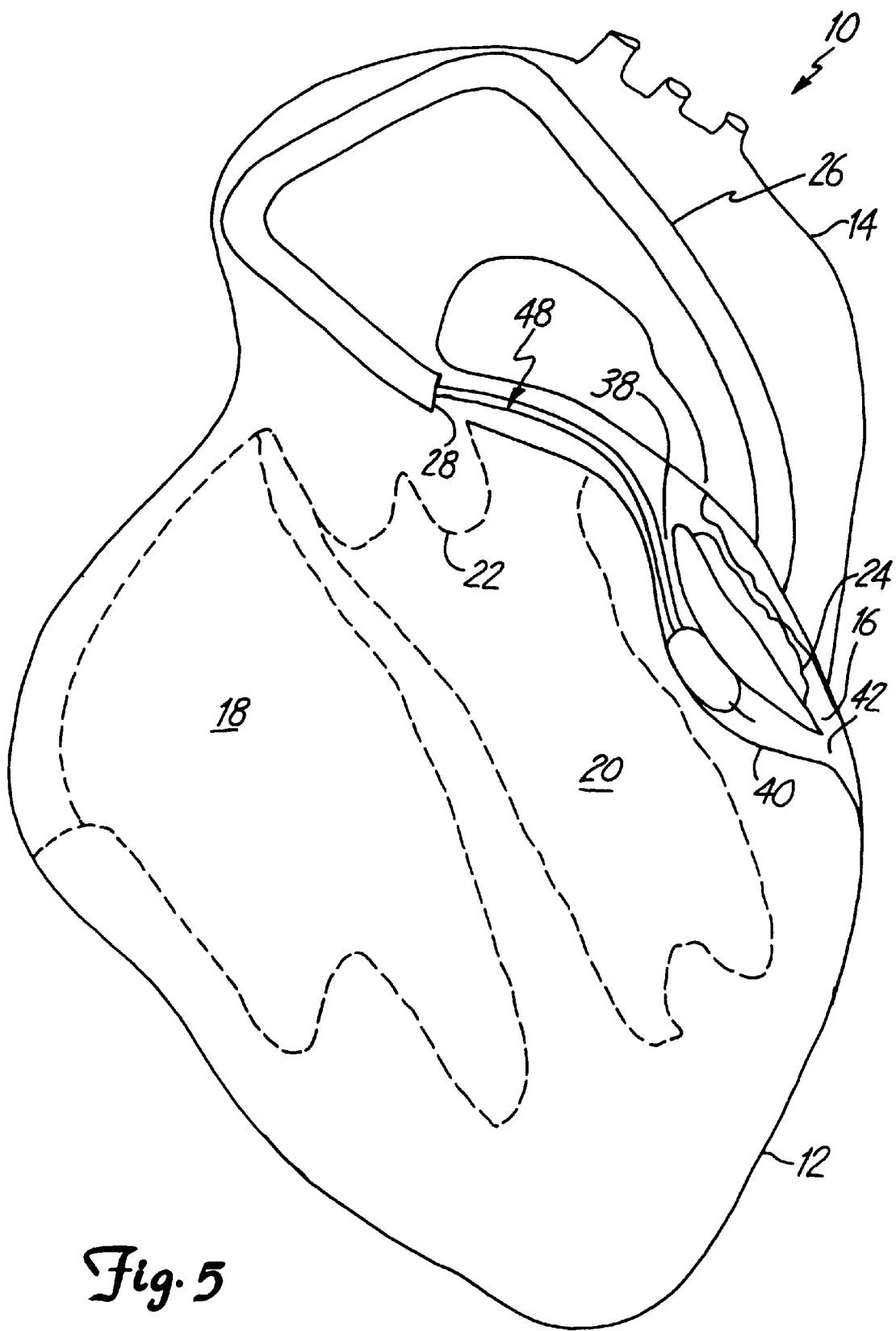
FIG. 5 illustrates deployment of a drug delivery device in the lumen through the heart tissue.

FIG. 5 illustrates another step in accordance with one preferred embodiment of the present invention. In FIG. 5, cutting device 32 has been withdrawn from vascular system 10 through guide catheter 26. Drug delivery device 48 has been advanced through guide catheter 28, through ostium 30 in vessel 16, through aperture 38 in vessel 16 and into lumen 40 through the heart tissue. Drug delivery device 48 is preferably any suitable and known drug delivery device, such as a microcatheter, a perforated balloon delivery device, or any other suitable device. In the preferred embodiment, drug delivery device 48 is used to deliver a drug to lumen 40 to enhance endothelial development in lumen 40. In one preferred embodiment, the substance delivered to lumen 40 with delivery device 48 includes a growth factor which enhances the growth of endothelial cells on the wall of lumen 40. In another preferred embodiment, the substance delivered to lumen 40 with delivery device 48 includes endothelial cells which enhance endothelialization in lumen 40.

Cutting device 32 can be guided through the heart tissue in any number of suitable ways from the point proximal of restriction 24 to the point distal of restriction 24 where it re-enters vessel 16. For instance, the cutting member 36 of cutting device 32 is preferably formed of radiopaque material or has radiopaque markings thereon. Therefore, when restriction 24 is not a total occlusion, contrast fluid is injected through vessel 16 to locate restriction 24. The relative position of the restriction 24 and cutting device 36 is then observed.

In another embodiment, radiopaque markers are placed in vessel 16 distal of restriction 24. Bi-plane fluoroscopy is then used to perform three dimensional visualization of the markers in vessel 16 and on cutting member 32 to bring them toward one another.

In another embodiment, restriction 24 is crossed with a conductive wire or fiber. Either the conductive wire or fiber residing in vessel 16 distal of restriction 24, or cutting device 32, are provided with a transmitter, and the other (either the wire or fiber which has been used to cross restriction 24, or cutting device 32) is provided with a receiver or sensor. In one preferred embodiment, the transmitter includes an array of active transmitters comprising one of ultrasound transmitters, radiofrequency transmitters, a plurality of point light sources, or a single intense point light source, or an electromagnetic transmitter (such as where current is actively applied to a coil to induce a magnetic field thereabout). The receiver, or sensor, is a suitable device which is compatible with the transmitter so that it can receive or sense the signals provided by the transmitter.

For instance, where the transmitter includes an inductive magnetic coil, the receiver includes a magnetic sensor array to receive the signals induced in the coil. When the transmitter includes an ultrasound transmitter, the receiver includes an ultrasound imager so that the relative positioning of the receiver device in the transmitter can be determined. When the transmitter includes a single point light source, or an array of point light sources, the receiver or sensor includes a photodiode array or an imaging fiber optic bundle which can detect the light emitted by the light sources. In addition, when the transmitter includes an RF transmitter, the receiver includes a directional antenna. In any of the above cases, or similar cases, the relative position between the transmitter and receiver can be determined so that the cutting member 36 of cutting device 32 can be properly located relative to vessel 16 such that it re-enters vessel 16 in a region distal of restriction 24.

It should also be noted that, in accordance with another preferred embodiment, lumen 40 is not formed such that it pierces vessel 16 in the region distal of restriction 24. Rather, vessel 40 is terminated just short of piercing the wall of vessel 16. In that case, blood carrying channels which have intersected the path of lumen 40 through the heart tissue are allowed to carry the blood to the tissue surrounding vessel 16. Further, the angiogenesis process which is part of the natural healing process can also develop branch vessels, arterioles, and capillaries from the site of lumen 40 to the tissue surrounding vessel 16, and angiogenesis can be stimulated by the introduction of growth factors.

It should also be noted that, in one preferred embodiment, rather than tunneling around restriction 24, cutting device 31 is advanced through vessel 16 and is used to form, or drill, orthogonal holes through the vessel wall into any or all of layers 15, 17, 19 and 21. The orthogonal holes provide relief for blood flow through and around restriction 24, and blood carrying channels which have been intersected by the path of the orthogonal holes through the tissue are allowed to carry the blood to the tissue surrounding vessel 16. Further, the angiogenesis process can also develop branch vessels, arterioles, and capillaries from the site of the orthogonal holes to the tissue surrounding vessel 16. Any suitable cutting device can be used to form the orthogonal holes, such as a mechanical drill-type device, or such as a laser reflected laterally within lumen 16.

Further, in one embodiment, blood flow through vessel 16 is stopped during the procedure. One system for stopping blood flow includes occluding balloons. Occluding balloons have a fairly low instance of emboli formation, and therefore have a fairly low instance of neurological problems which result from the formation of emboli.

Thus, it can be seen that, by tunneling through the vessel wall and heart tissue to form a lumen therethrough which communicates between the proximal and distal ends of vessel 16, around restriction 24, restriction 24 is effectively bypassed. The tunnel can also be formed directly from the aorta to a region in the restricted lumen distal of restriction 24. This is accomplished without the need for open heart surgery and its associated disadvantages.

Although the present invention has been described with reference to preferred embodiments, workers skilled in the art will recognize that changes may be made in form and detail without departing from the spirit and scope of the invention.

What is claimed is:

1. A method of bypassing a restriction in a coronary parent vessel lying adjacent heart tissue in a heart, the heart communicating with an aorta, the method comprising:
   accessing a first region of the coronary parent vessel on a first side of the restriction;
   forming a first aperture in the coronary parent vessel in the first region;
   forming a lumen through the heart tissue, the lumen communicating with the coronary parent vessel through the first aperture; and
   forming a second aperture in a second region of the coronary parent vessel on a second side of the restriction such that the lumen through the heart tissue communicates with the coronary parent vessel through the second aperture.

2. The method of claim 1 and further comprising:
   delivering a substance to the lumen in the heart tissue to increase endothelialization in the lumen in the heart tissue.

3. The method of claim 2 wherein the substance is growth factor.

4. The method of claim 2 wherein the substance is endothelial cells.

5. The method of claim 1 wherein forming the first aperture comprises:
   forming the first aperture in a region proximal of the restriction.

6. The method of claim 1 wherein forming a second aperture comprises:
   forming the second aperture in a region distal of the restriction, by accessing a wall of the coronary parent vessel from the lumen in the heart tissue.

7. The method of claim 1 wherein accessing a first region of the coronary parent vessel comprises:
   advancing a guide catheter through the aorta such that the distal end of the guide catheter lies proximate an ostium of the coronary parent vessel; and
   advancing a cutting device through the guide catheter and into the coronary parent vessel proximate the first region in the coronary parent vessel.

8. A method of bypassing a restriction in a coronary parent vessel lying adjacent heart tissue in a heart, the heart communicating with an aorta, the method comprising:
   accessing a first region of the coronary parent vessel on a proximal side of the restriction;
   forming a first aperture in the coronary parent vessel in the first region;
   forming a lumen through the heart tissue, the lumen communicating with the coronary parent vessel through the first aperture, the lumen extending from the first aperture to a region proximate the coronary parent vessel distal of the restriction.

9. The method of claim 8 and further comprising:
   extending the lumen to form a second aperture in a second region of the coronary parent vessel distal of the restriction such that the lumen through the heart tissue communicates with the coronary parent vessel through the first and second apertures, around the restriction, bypassing the restriction.

10. The method of claim 9 and further comprising:
    delivering a substance to increase endothelialization in the lumen in the heart tissue.

11. The method of claim 10 wherein the substance is growth factor.

12. The method of claim 10 wherein the substance is endothelial cells.

13. The method of claim 9 wherein accessing a first region of the coronary parent vessel comprises:
    advancing a guide catheter through the aorta such that the distal end of the guide catheter is located proximate an ostium of the coronary parent vessel; and
    advancing a cutting device through the guide catheter and through the coronary parent vessel to the first region of the coronary parent vessel.

14. A method of bypassing a restriction in a coronary parent vessel lying adjacent heart tissue in a heart, the heart communicating with an aorta, the method comprising:
    accessing a first region of the coronary parent vessel proximal of the restriction; and
    forming a first aperture in the coronary parent vessel in the first region to access the heart tissue;

forming a lumen through the heart tissue to a region proximate the coronary parent vessel distal of the restriction; and forming a second aperture in the coronary parent vessel distal of the restriction such that the lumen through the heart communicates with the aorta and with the coronary parent vessel through the first and second aperture in the parent vessel.

15. The method of claim 14 and further comprising:

delivering a substance to increase endothelialization in the lumen in the heart tissue.

16. The method of claim 15 wherein the substance is growth factor.

17. The method of claim 15 wherein the substance is endothelial cells.

18. The method of claim 14 wherein accessing a first region of the coronary parent vessel comprises:

advancing a guide catheter through the aorta such that the distal end of the guide catheter is located proximate an ostium of the coronary parent vessel; and advancing a cutting device through the guide catheter and through the coronary parent vessel to the first region of the coronary parent vessel.

19. The method of claim 14 wherein forming an aperture in the coronary parent vessel distal of the occlusion comprises:

forming the aperture distal of the restriction from within the lumen in the heart tissue.

* * * * *